(12) United States Patent
Heide et al.

(10) Patent No.: US 10,620,029 B2
(45) Date of Patent: Apr. 14, 2020

(54) FLOWMETER AND CASSETTE MODULE FOR A FLOWMETER

(71) Applicant: Fresenius Medical Care Deutschland GmbH, Bad Homburg (DE)

(72) Inventors: Alexander Heide, Eppstein (DE); Dejan Nikolic, Schwalbach am Taunus (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 9 days.

(21) Appl. No.: 15/125,274

(22) PCT Filed: Jun. 16, 2015

(86) PCT No.: PCT/EP2015/063427
§ 371 (c)(1),
(2) Date: Sep. 12, 2016

(87) PCT Pub. No.: WO2015/197424
PCT Pub. Date: Dec. 30, 2015

(65) Prior Publication Data
US 2017/0074706 A1 Mar. 16, 2017

(30) Foreign Application Priority Data
Jun. 25, 2014 (DE) .......................... 10 2014 009 444

(51) Int. Cl.
*G01F 15/14* (2006.01)
*G01F 1/58* (2006.01)
*A61M 1/16* (2006.01)

(52) U.S. Cl.
CPC ........... *G01F 15/14* (2013.01); *A61M 1/1647* (2014.02); *G01F 1/58* (2013.01); *A61M 2205/12* (2013.01);
(Continued)

(58) Field of Classification Search
CPC . G01F 15/14; G01F 1/58; A61M 1/14; A61M 1/1647
See application file for complete search history.

(56) References Cited

U.S. PATENT DOCUMENTS 4,585,552 A 4/1986 Gummesson et al.
4,902,282 A 2/1990 Bellotti et al.
(Continued)

FOREIGN PATENT DOCUMENTS

CN 102844057 12/2012
DE 1573007 6/1970
(Continued)

*Primary Examiner* — David M. Gray
*Assistant Examiner* — Andrew V Do
(74) *Attorney, Agent, or Firm* — Jacobson Holman, PLLC.

(57) ABSTRACT

A cassette module (19, 29, 319, 419, 59, 69) for a differential flowmeter is disclosed, wherein the cassette module (19, 29, 319, 419, 59, 69) forms a first fluid-carrying channel (16, 216, 316, 611, 615) and the second fluid-carrying channel (17, 217, 317, 610, 616) during operation of the differential flowmeter. The cassette module is specific in the regard that a geometric deformation of the channels due to a temperature difference between the channels (16, 216, 316, 611, 615, 17, 217, 317, 610, 616) is minimized or prevented. In addition a differential flowmeter containing the cassette module (19, 29, 319, 419, 59, 69) disclosed here is also described.

10 Claims, 3 Drawing Sheets

(52) U.S. Cl.
CPC ............... *A61M 2205/3317* (2013.01); *A61M 2205/3334* (2013.01)

(56) References Cited

U.S. PATENT DOCUMENTS

| | | | |
|---|---|---|---|
| 2012/0095537 A1 | 4/2012 | Hall et al. | |
| 2013/0075314 A1* | 3/2013 | Nikolic | A61M 1/14 210/143 |
| 2016/0074565 A1* | 3/2016 | Giordano | A61M 1/1605 210/85 |

FOREIGN PATENT DOCUMENTS

| | | |
|---|---|---|
| DE | 1951378 | 4/1971 |
| DE | 102010003642 | 9/2011 |
| EP | 2169359 | 3/2010 |
| GB | 2056691 | 3/1981 |
| WO | WO 2008056976 | 5/2008 |
| WO | WO 2013175547 | 11/2013 |
| WO | WO 2015/197424 | 12/2015 |

\* cited by examiner

FLOWMETER AND CASSETTE MODULE FOR A FLOWMETER

TECHNICAL FIELD

The invention relates to a flowmeter, in particular a differential flowmeter for measuring the difference between a first fluid flow and a second fluid flow. The invention also relates to a cassette module having channels for the first and second fluid flows, for use in a differential flowmeter.

BACKGROUND

To remove liquid and the substances that must be eliminated in urine, various methods of purifying and/or treating blood with machines have been used to treat chronic renal failure. Diffusive mass transport is predominant in hemodialysis (HD), and convective mass transport through the membrane occurs in hemofiltration (HF). Hemodiafiltration (HDF) is a combination of these two methods. In peritoneal dialysis (PD), no extracorporeal circulation is needed and the peritoneum is used as a contact membrane.

Because of the large exchange quantities, it is necessary to accurately balance the fluid withdrawn, on the one hand, with the fluid supplied, on the other hand, as well as the volume to be subjected to ultrafiltration over the total treatment time with the known methods an also with continuous arteriovenous HF, continuous venovenous HF and plasma filtration (PF). Gravimetric and volumetric balancing systems are known in the prior art.

In addition, there are also known methods, which measure the fluid flows of the fluids flowing into the dialyzer and the fluids flowing out of the dialyzer continuously and balance them with respect to one another. Flow measurement sensors or flowmeters of various designs are used for this purpose.

Magnetic flowmeters, which are also known as electromagnetic flowmeters or inductive flowmeters are based on the measurement of the velocity of flow of a conductive fluid through a known or controlled magnetic field by measuring the induced electric voltage. With a known flow cross section, the flow rate or the volume flow can be deduced from the velocity of flow, and then must be covered by the concept of fluid flow in the following discussion. An electric voltage occurs in a magnetic field through which a flow passes through a charge separation of the ions which are present in a conductive fluid and can be measured as the induced voltage. The voltage measurement is typically performed by deriving the induced voltage from a pair of electrodes which in electric contact with the conductive fluid or which are linked capacitively to the fluid. This voltage is proportional to the velocity of flow and depends on the magnetic field strength. The charge separation takes place in the direction perpendicular to the direction of flow and to the direction of the magnetic field. The magnetic field of a magnetic flow mater is therefore preferably disposed perpendicular to the direction of flow in the corresponding fluid channel, and the electrode pair for diverting the induced electric voltage is preferably disposed perpendicular to the magnetic field and also perpendicular to the direction of flow in the fluid channel.

A typical electromagnetic flowmeter is constructed from a nonmagnetic and nonmagnetizable pipe, which is lined with an electrically insulating material on the inside.

The magnetic field is typically generated by one or more coils disposed outside of the tube through which the fluid flows. The electric voltage induced by the fluid flow is typically determined by a voltmeter. The result of the voltage measurement is sent to an evaluation unit for determining the fluid flow, i.e., the flow rate or the volume flow based on the measured voltage.

If an electromagnetic flowmeter is designed as a differential flowmeter for measuring a flow difference between a first and a second fluid-carrying channel, then advantageously a joint magnetic field will penetrate through the first and second fluid-carrying channels.

If the first and second fluid-carrying channels correspond to one another with regard to their geometric dimensions, then the voltage difference between a first electrode pair disposed on the first fluid-carrying channel and a second electrode pair disposed on the second fluid-carrying channel indicates directly the difference between the flow in the first channel and the flow in the second channel. If the first and second electrode pairs are connected in series, this voltage difference can be picked up directly.

An electromagnetic differential flowmeter is advantageously constructed from the one cassette module in which the fluid-carrying channels are formed, each having an electrode pair, an electromagnet or permanent magnet for generating a magnetic field between the electrode pairs and an evaluation unit for evaluating the voltages or the differential voltage between the electrode pairs.

The cassette module in which the fluid-carrying channels are formed is advantageously designed as a disposable part, for example as part of a dialysis fluid circulation.

The cassette module may or may not have additional elements of the dialysis fluid circulation as part of a dialysis fluid circulation.

The inventors of the present invention have recognized that a temperature difference between the first fluid-carrying channel and the second fluid-carrying channel can lead to a reduced precision of the differential flowmeter.

Therefore the object of the present invention is to provide improved balancing of the fluid flows.

SUMMARY

This object is achieved by a cassette module according to claim 1 as well as by a differential flowmeter according to claim 10. Advantageous refinements are defined in the dependent claims.

In accordance with the teaching of the present invention, a cassette module for a differential flowmeter is made available. The differential flowmeter contains:
a cassette module with a first and a second channel,
a magnet for generating a magnetic field in the first and second channels,
each with an electrode pair disposed on the cassette module for tapping an electric voltage at the first and second channels when the fluid flows through the first and/or second channels, so that a difference in the derived voltages indicates a difference between a fluid flow through the first channel and through the second channel.

The cassette module is designed so that a geometric deformation of the channels due to a temperature difference between the first channel and the second channel is largely ruled out or at least minimized. Due to the fact that a geometric deformation of the channels is ruled out or minimized, the position relationships between the electrodes and the magnetic field are maintained when a temperature difference prevails between the first channel and the second channel.

A constant positional relationship between the electrodes and the magnetic field contributes toward an increased measurement accuracy of the differential flowmeter.

Deformation of the channels during operation of the differential flowmeter can be essentially ruled out or reduced by the fact that the cassette module forms a base body to which the fluid-carrying channels are attached, wherein the geometric deformation is minimized by a reinforcing structure of the base body. The reinforcing structure is advantageously ensured by the fact that the base body is designed to be solid and therefore the base body itself forms a reinforcing structure. In an alternative embodiment of the cassette module, the reinforcing structure is formed by reinforcing ribs.

A deformation of the channels can also be ruled out or minimized by the fact that an insulation layer for thermal insulation of the channels is provided between the channels. The insulation layer may be made of an insulation material that functions as a thermal insulator, for example a ceramic or a foam material. In an alternative embodiment, a recess is provided between the channels so that the channels are insulated by the layer of air situated between them.

In an advantageous embodiment of the cassette module, the change in measured values occurring due to deformation of the channels amounts to less than 0.05 percent per degree Kelvin temperature difference between the channels.

In another advantageous embodiment, the geometric deformation is minimized or prevented by the fact that a contact zone between the first and second channels is minimized. The regions of the channels in which the first and second channels approach one another are regarded as the contact zone. This region will in general be the region in which the common magnetic field penetrates through the first and second channels and in which the electrode pairs are disposed.

The contact zone between the first and second channels is minimized in an advantageous embodiment by the fact that the first and second channels are disposed essentially perpendicular to one another.

In another embodiment of the cassette module, at least two first channels and at least two second channels are provided, the channels being disposed in such a way that mechanical stresses due to a temperature difference between the first and second channels are compensated.

For example, two first channels may be provided for one direction of flow and two second channels may be provided for the opposite direction of flow, such that the total of four channels are disposed parallel to one another and the two first channels and the two second channels are each opposite one another.

Such a configuration then also leads to little or no deformation when a particular reinforcing structure is provided. Such a configuration therefore saves on material in particular.

In one embodiment, the cassette module is part of a dialysis fluid circulation, and the differential flowmeter is provided for balancing dialysis fluid between an incoming flow of fresh dialysis fluid to a blood treatment unit and an outgoing flow for spent dialysis fluid. In one advantageous embodiment, the cassette module contains additional elements of a dialysis fluid circulation such as a dialysis fluid pump, for example.

In one advantageous embodiment, the cassette module is provided for use as a disposable article.

DETAILED DESCRIPTION OF THE DRAWINGS

Figure 1:
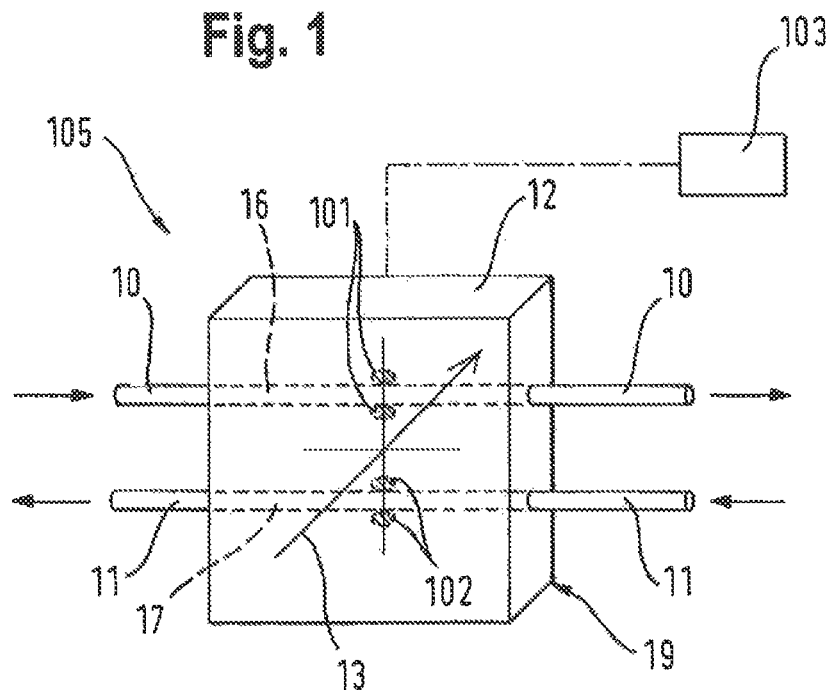
FIGS. 1-6 show different embodiments of a cassette module for a differential flowmeter.

FIG. 1 shows one embodiment of a cassette module 19 for a differential flowmeter. The cassette module 19 has a solid base body 12 in which channels 16, 17 are formed, carrying fluid when the differential flowmeter is operated. Fluid-carrying lines 10, 11 are connected to the fluid-carrying channels 16, 17. In one embodiment the differential flowmeter is part of a balancing unit 105 for balancing dialysis fluid in a dialysis fluid circulation. In this case the lines 10, 11 as well as the channels 16, 17 are part of a dialysis fluid circulation.

The channels 16, 17 are penetrated by a magnetic field 13 which is generated by a magnet (not shown). The magnetic field is essentially perpendicular to the direction of flow in the channels 16, 17. Electrodes 101, 102 are disposed on the channels 16, 17, essentially perpendicular to the magnetic field 13 and to the direction of flow in the channels 16, 17, tap a voltage transversely to the respective direction of flow. The electrodes are connected to an evaluation unit 103 which determines a difference in the fluid flows in the channels and thus a fluid balance between the fluid-carrying lines based on the tapped voltages, in particular based on a difference in the derived voltages.

Due to the solid design of the base body 12, a reinforcing structure is provided, minimizing the geometric deformation of the base body due to a temperature difference between the lines 10, 11. In an alternative embodiment, a reinforcing structure may also be formed by reinforcing ribs.

Figure 2:
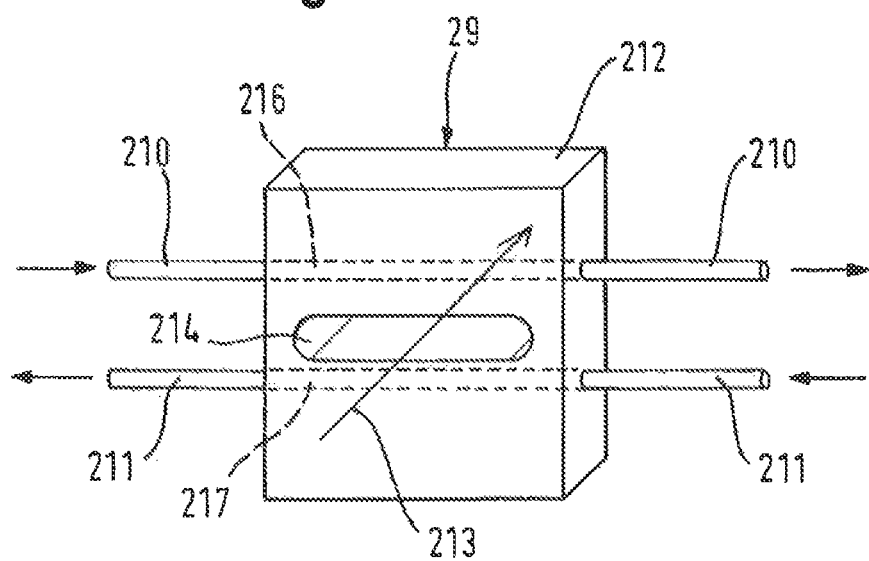

FIG. 2 shows an alternative embodiment of a cassette module 29 for a differential flowmeter. The cassette module 29 has a base body 212 in which channels 216, 217 which are fluid-carrying are formed when the differential flowmeter is operated. Fluid-carrying lines 210, 211 are connected to the fluid-carrying channels 216, 217. The channels 216, 217 are permeated by a magnetic field 213. Voltages tapped at electrodes that are not shown in greater detail here are induced by the magnetic field 213 and permit the determination of a fluid balance corresponding to the configuration already described with regard to FIG. 1.

The base body forms a recess 214 between the fluid-carrying channels 216 and 217 which forms an insulation layer for thermal insulation of the channels. The recess may be filled with a thermal insulation material such as ceramic or a foam. In an alternative embodiment, insulation of the channels is provided by the fact that the air layer situated between the channels has an insulating effect. The insulation between channel 216 and channel 217 results in minimization of any geometric deformation of the base body due to a temperature difference between the lines 216 and 217.

Figure 3:
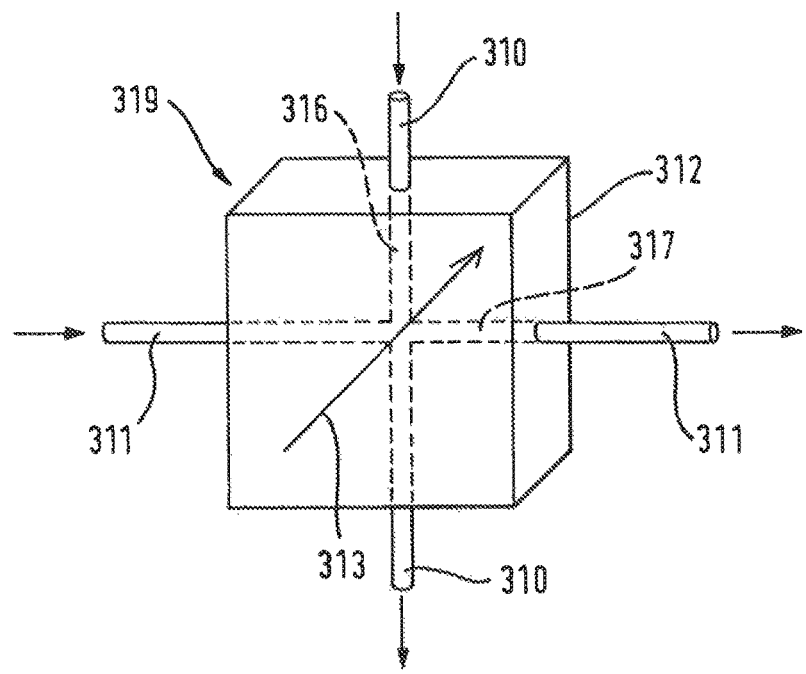

FIG. 3 shows another alternative embodiment of a cassette model 319 for a differential flowmeter. The cassette module 319 has a base body 312 in which channels 316, 317, which are fluid-carrying when the differential flowmeter is being operated, are formed. Fluid-carrying lines 310, 311 are connected to the fluid-carrying channels 316, 317. A magnetic field generated by magnets (not shown) permeates the first and second channels in a contact zone. Electrodes for diverting voltages induced on the electrodes are also disposed in this region. Voltages derived at the electrodes make it possible to determine a fluid balance corresponding to the configuration already described in conjunction with FIG. 1.

The contact zone between the first and second channels is minimized or prevented in an advantageous embodiment by the fact that the first and second channels are disposed essentially at right angles to one another.

The minimized contact zone between the channel 316 and the channel 317 has the result that any geometric deformation of the base body due to a temperature difference between the lines 216 and 217 is minimized.

Figure 4:
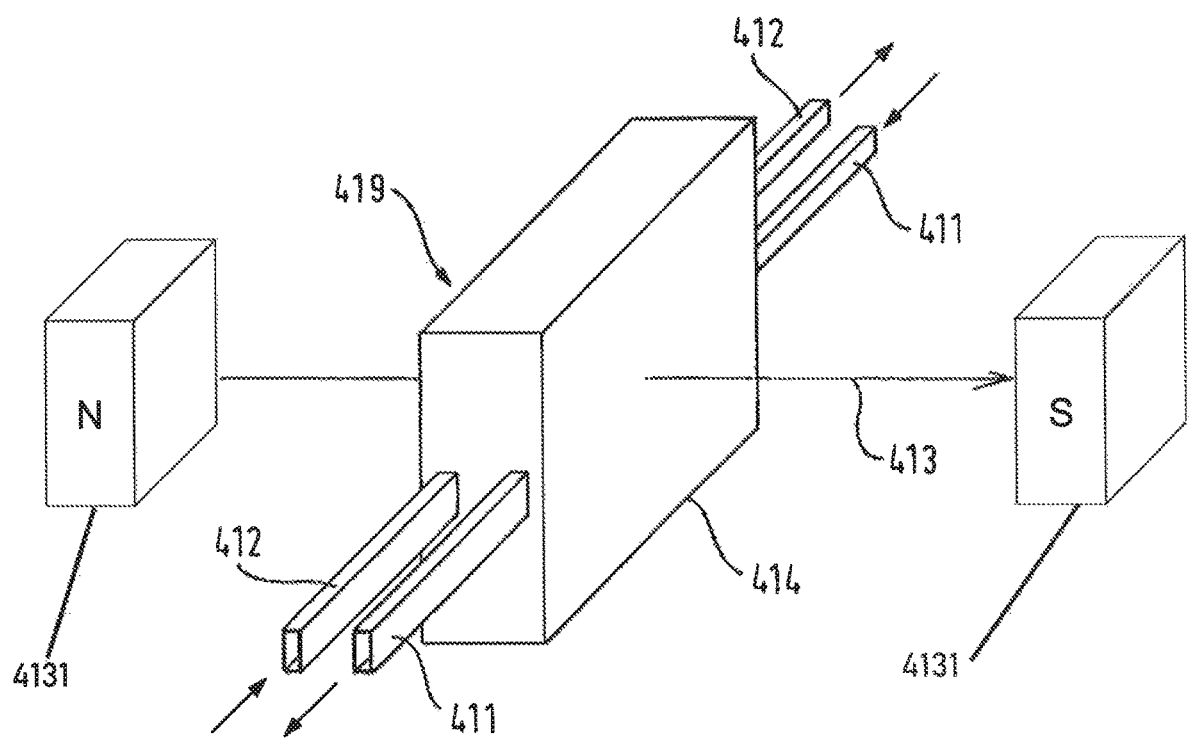

FIG. 4 shows an alternative design of a cassette module 419 for a differential flowmeter. The cassette module 419 has a base body 414 in which a first channel and a second channel, which are fluid-carrying when the differential flowmeter is in operation, are formed. These channels are part of the fluid-carrying lines 411, 412 and are permeated by a magnetic field 413 which is generated by a magnet 4131. The magnetic field is essentially perpendicular to the direction of flow in the channels.

Voltages induced by the magnetic field 413 and tapped at electrodes (not shown in detail here) make it possible to determine a fluid balance according to the configuration already described in conjunction with FIG. 1.

A certain magnetic field line permeates both the first and second channels. Therefore, essentially the same magnetic field prevails in the first channel as in the second channel. This permits a particularly accurate determination of the fluid balance.

The cassette module corresponds to the cassette module described in conjunction with FIG. 1 inasmuch as the base body has a solid design. Due to the solid design of the base body, a reinforcing structure is provided, minimizing any geometric deformation of the base body due to a temperature difference between the lines 411, 412.

Figure 5:
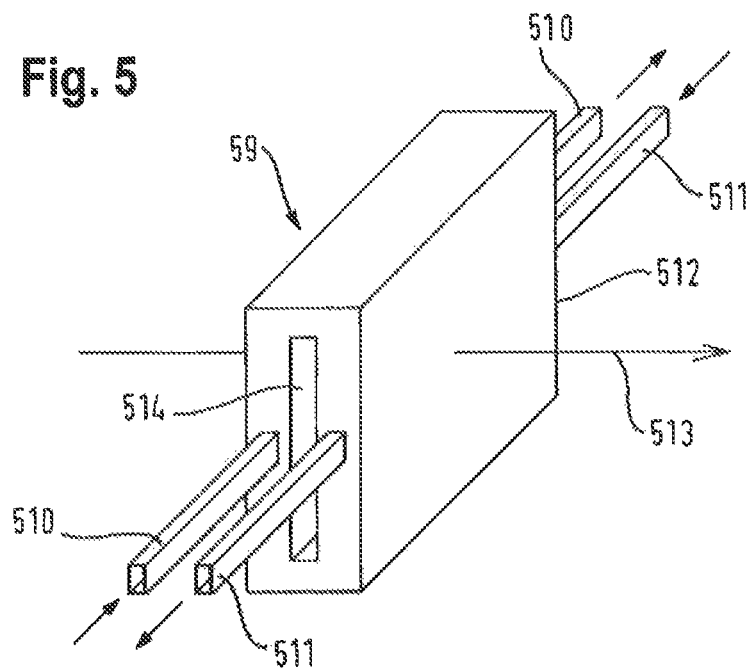

FIG. 5 shows another alternative embodiment of cassette module 59 for a differential flowmeter. The cassette module has a base body 512 which forms a first and a second channel, each being part of the fluid-carrying lines 510, 511.

The channels are permeated by a magnetic field 513, which is generated by a magnet (not shown). The magnetic field is essentially at a right angle to the direction of flow in the channels.

Voltages induced by the magnetic field 513 and tapped at electrodes, which are not shown in detail, permit determination of a fluid balance corresponding to the configuration already described in relation to FIG. 1.

A certain magnetic field line passes through both the first and the second channels. Therefore, essentially the same magnetic field prevails in the first channel as in the second channel. This permits a particularly accurate determination of the fluid balance.

The cassette module has a recess 514 in the base body 512 for thermal insulation of the channels. The recess can be filled with a thermal insulation material such as ceramic or a foam. In an alternative embodiment, insulation of the channels is provided by the fact that the air layer situated between the channels has an insulating effect.

The insulation between the first channel and the second channel causes a geometric deformation of the base body due to a temperature difference between the lines 510 and 511 to be minimized.

Figure 6:
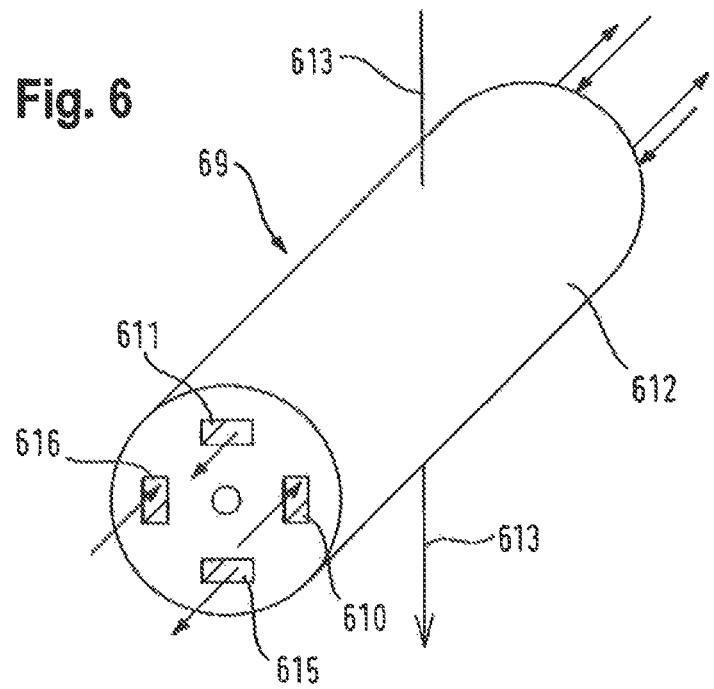

FIG. 6 shows an alternative embodiment of a cassette module 612 for a differential flowmeter. The cassette module 69 has a base body 612 in which first channels 611 and 615 and second channels 610, 616 are formed; these are fluid-carrying channels when the differential flowmeter is in operation. The first channels are part of a first line which is a fluid-carrying line during operation of the differential flowmeter, such that the line splits into the two first channels, and the second channels are part of a second line which is fluid-carrying during operation of the differential flowmeter and splits into the two second channels.

In other words, the directions of flow in the two first channels correspond to one another, and the directions of flow in the two second channels correspond to one another. The fluid flows in the same direction through opposing channels.

The configuration of channels has the result that mechanical stresses caused by a prevailing temperature difference between the first line and the second line corresponding to a temperature difference between the two first channels and the two second channels are equalized.

The channels 611, 610, 616, 615 are permeated by a magnetic field 613 which is generated by a magnet (not shown). The magnetic field is essentially perpendicular to the direction of flow in the channels 611, 610, 616, 615.

Electrodes (not shown) are disposed on the channels 611, 610, 616, 615 so that they are essentially perpendicular to the magnetic field 613 and to the direction of flow in the channels 611, 610, 616, 615 in order to tap a voltage transversely to the respective direction of flow.

The electrodes are connected to an evaluation unit (not shown) which indicates a difference between the fluid flow in the first line and the fluid flow in the second line and thus in the case of fluid balance between the first and second lines based on the voltages thereby tapped.

Voltages tapped at the electrodes of the first channels are each added to obtain a total voltage at the two first channels, and voltages tapped at the electrodes of the second channels are added to obtain a total voltage at the two second channels. The two total voltages are then subtracted one from the other.

In an alternative embodiment, electrode pairs are provided at only one of the first channels and one of the second channels.

Such a configuration then also leads to little or no deformation when no particular reinforcing structure is provided. Therefore, such a configuration is particularly sparing of materials.

In an advantageous embodiment of the cassette module, the change in measured value attributed to the deformation of the channels amounts to less than 0.05 percent per degree Kelvin.

The following rule also holds for all embodiments: Due to the fact that geometric deformation of the channels is prevented or minimized, the position relationships between the electrodes and the magnetic field are preserved when a temperature difference prevails between the first and second lines. A constant position relationship between electrodes and the magnetic field contributes toward an improved measurement accuracy of the differential flowmeter.

The invention claimed is:

1. A cassette module for a differential flowmeter, the cassette module comprising a base body, a first fluid-carrying channel through the base body, and a second fluid-carrying channel through the base body, characterized in that geometric deformation of the first and second fluid-carrying channels due to a temperature difference between the first and second fluid-carrying channels during operation is minimized or prevented by a configuration selected from the group consisting of the first fluid-carrying channel disposed through the base body essentially at a right angle to the second fluid-carrying channel through the base body such that a contact zone between the first fluid-carrying channel and the second fluid-carrying channel in the base body is minimized, and providing at least two of the first fluid-carrying channels and at least two of the second fluid-carrying channels, wherein the at least two first fluid-carrying channels are disposed reciprocally to the at least two second fluid-carrying channels, respectively, so that mechanical stresses due to temperature differences are equalized.

2. The cassette module according to claim 1, wherein the at least two first fluid-carrying channels are disposed reciprocally to the at least two second fluid-carrying channels, respectively, in mirror symmetry.

3. The cassette module according to claim 1, wherein the geometric deformation of the first and second fluid-carrying channels amounts to less than 0.05 percent per degree Kelvin.

4. The cassette module according to claim 1, designed as a disposable component for a differential flowmeter.

5. A differential flowmeter for balancing between fluid flows, comprising:
a cassette module according to claim 1,
a magnet for generating a magnetic field in the first fluid-carrying channel and in the second fluid-carrying channel of the cassette module,
an electrode pair for tapping an electric voltage at the first fluid-carrying channel and at the second fluid-carrying channel, when the fluid flows through the first and/or the second fluid-carrying channel so that a difference between the tapped voltages is indicative of a difference between a fluid flow through the first fluid-carrying channel and through the second fluid-carrying channel.

6. The differential flowmeter according to claim 5, further comprising an evaluation unit for determining the difference between the voltage tapped at the first fluid-carrying channel and the voltage tapped at the second fluid-carrying channel and for determining the difference in the fluid flows based on the certain voltage difference.

7. A cassette module for a differential flowmeter, the cassette module comprising a base body, a first fluid-carrying channel through the base body, and a second fluid-carrying channel through the base body, characterized in that geometric deformation of the first and second fluid-carrying channels due to a temperature difference between the first and second fluid-carrying channels during operation is minimized or prevented by a configuration selected from the group consisting of
the first fluid-carrying channel disposed through the base body essentially at a right angle to the second fluid-carrying channel through the base body such that a contact zone between the first fluid-carrying channel and the second fluid-carrying channel in the base body is minimized, and
providing at least two of the first fluid-carrying channels and at least two of the second fluid-carrying channels, wherein the at least two first fluid-carrying channels are disposed reciprocally to the at least two second fluid-carrying channels, respectively, so that mechanical stresses due to temperature differences are equalized, wherein the at least two first fluid-carrying channels are disposed reciprocally to the at least two second fluid-carrying channels, respectively, in mirror symmetry.

8. A cassette module for a differential flowmeter, the cassette module comprising a base body, a first fluid-carrying channel through the base body, and a second fluid-carrying channel through the base body, characterized in that geometric deformation of the first and second fluid-carrying channels due to a temperature difference between the first and second fluid-carrying channels during operation is minimized or prevented by a configuration selected from the group consisting of
the first fluid-carrying channel disposed through the base body essentially at a right angle to the second fluid-carrying channel through the base body such that a contact zone between the first fluid-carrying channel and the second fluid-carrying channel in the base body is minimized, and
providing at least two of the first fluid-carrying channels and at least two of the second fluid-carrying channels, wherein the at least two first fluid-carrying channels are disposed reciprocally to the at least two second fluid-carrying channels, respectively, so that mechanical stresses due to temperature differences are equalized, and wherein the geometric deformation of the first and second fluid-carrying channels amounts to less than 0.05 percent per degree Kelvin.

9. A differential flowmeter for balancing between fluid flows, comprising:
a cassette module for a differential flowmeter, the cassette module comprising a base body, a first fluid-carrying channel through the base body, and a second fluid-carrying channel through the base body, characterized in that geometric deformation of the first and second fluid-carrying channels due to a temperature difference between the first and second fluid-carrying channels during operation is minimized or prevented by a configuration selected from the group consisting of
a layer of thermal insulation provided between the first fluid-carrying channel and the second fluid-carrying channel,
the first fluid-carrying channel disposed through the base body essentially at a right angle to the second fluid-carrying channel through the base body such that a contact zone between the first fluid-carrying channel and the second fluid-carrying channel in the base body is minimized, and
providing at least two of the first fluid-carrying channels and at least two of the second fluid-carrying channels, wherein the at least two first fluid-carrying channels are disposed reciprocally to the at least two second fluid-carrying channels, respectively, so that mechanical stresses due to temperature differences are equalized,
a magnet for generating a magnetic field in the first fluid-carrying channel and in the second fluid-carrying channel of the cassette module, and
an electrode pair for tapping an electric voltage at the first fluid-carrying channel and at the second fluid-carrying channel, when the fluid flows through the first and/or the second fluid-carrying channel so that a difference between the tapped voltages is indicative of a difference between a fluid flow through the first fluid-carrying channel and through the second fluid-carrying channel.

10. The differential flowmeter according to claim 9, further comprising an evaluation unit for determining the difference between the voltage tapped at the first fluid-carrying channel and the voltage tapped at the second fluid-carrying channel and for determining the difference in the fluid flows based on the certain voltage difference.

* * * * *